US012211335B2

(12) United States Patent
Hurd et al.

(10) Patent No.: US 12,211,335 B2
(45) Date of Patent: Jan. 28, 2025

(54) REMOTE BEVERAGE CARTRIDGE SYSTEM

(71) Applicant: SUM LLC, Birmingham, AL (US)

(72) Inventors: Tyler Hurd, Birmingham, AL (US); Stuart Griffin, Birmingham, AL (US); Diego Solano, Oakland, CA (US); Josh Torres, Birmingham, AL (US); Joseph S. Bird, III, Hoover, AL (US)

(73) Assignee: SUM LLC, Birmingham, AL (US)

( * ) Notice: Subject to any disclaimer, the term of this patent is extended or adjusted under 35 U.S.C. 154(b) by 0 days.

(21) Appl. No.: 18/144,036

(22) Filed: May 5, 2023

(65) Prior Publication Data

US 2023/0360465 A1    Nov. 9, 2023

Related U.S. Application Data

(60) Provisional application No. 63/338,867, filed on May 5, 2022.

(51) Int. Cl.
*G07F 13/06* (2006.01)
*A47J 31/40* (2006.01)
(Continued)

(52) U.S. Cl.
CPC .......... *G07F 13/065* (2013.01); *A47J 31/407* (2013.01); *A47J 31/4492* (2013.01); *A47J 31/521* (2018.08); *A47J 31/5251* (2018.08); *A47J 31/5253* (2018.08); *A47J 31/5255* (2018.08); *A47J 31/60* (2013.01); *A61B 5/1118* (2013.01); *G06Q 20/18* (2013.01); *G06Q 30/0631* (2013.01); *G07F 13/025* (2013.01); *A47J 2202/00* (2013.01)

(58) Field of Classification Search
CPC .. A47J 31/521; A47J 31/5251; A47J 31/5253; A47J 31/407; A47J 31/4492; A47J 31/60; A47J 31/5255
USPC ..................................... 99/280, 295
See application file for complete search history.

(56) References Cited

U.S. PATENT DOCUMENTS

| 8,863,649 | B1 | 10/2014 | Rao et al. | |
|---|---|---|---|---|
| 2012/0104026 | A1* | 5/2012 | Hortin | A47J 31/401 99/275 |

(Continued)

FOREIGN PATENT DOCUMENTS

| KR | 10-2016-0104703 A | 9/2016 | |
|---|---|---|---|
| WO | WO-2016029294 A1 * | 3/2016 | ............ A47J 31/404 |

OTHER PUBLICATIONS

International Search Report and Written Opinion received for International Patent Application No. PCT/US2023/021251, mailed on Sep. 4, 2023, 9 pages.

*Primary Examiner* — Nathaniel E Wiehe
*Assistant Examiner* — Alba T Rosario-Aponte
(74) *Attorney, Agent, or Firm* — Joseph S. Bird, III (57) ABSTRACT

Disclosed is a remote cartridge system for managing concentrate cartridges, both for beverages and cleaning, and the dispenser in which they are installed. Each cartridge contains specific cartridge information which is communicated to a controller of a dispenser allowing remote supervision of maintenance, inventory, cleaning and revision of firmware. The system has a web domain and a mobile app for a smart mobile device which are synchronized, the web domain communicating directly with the controller or indirectly through the smart mobile device.

14 Claims, 9 Drawing Sheets

(51) Int. Cl.
*A47J 31/44* (2006.01)
*A47J 31/52* (2006.01)
*A47J 31/60* (2006.01)
*A61B 5/11* (2006.01)
*G06Q 20/18* (2012.01)
*G06Q 30/0601* (2023.01)
*G07F 13/02* (2006.01)

(56) References Cited

U.S. PATENT DOCUMENTS

| | | |
|---|---|---|
| 2015/0183627 A1 | 7/2015 | Tansey, Jr. |
| 2017/0066638 A1 | 3/2017 | Gatipon |
| 2017/0215632 A1* | 8/2017 | Tinkler ............... A47J 31/407 |
| 2018/0177325 A1* | 6/2018 | Lyons ............... A47J 31/401 |
| 2020/0122994 A1 | 4/2020 | Cimatti et al. |
| 2021/0300804 A1* | 9/2021 | Broga ............... D06F 39/088 |

\* cited by examiner

| City | Location | Dispenser ID | Flavor ID | Cartridge Status | Service Status | Daily Usage | Cartridge days left | Notifications |
|---|---|---|---|---|---|---|---|---|
| HSV | WWW | #456345 | #2 Watermelon 13681992 | 32% Low Level | In Transit | 3 | 2 | *TODAY*<br>Position Change<br>Cartridge ID Changed Dispenser #456345 at WWW in Huntsville has Changed the cartridge ID in #5 position to Mango |
| | | | #3 Pineapple 13681993 | 0% Empty | Out of Stock | 2.5 | 0 | |
| | | | #4 Cranberry 13681995 | 24% Low Level | In Transit | 3.6 | 1 | |
| | | | #5 Mango 13681994 | 78% Normal | OK | 1.1 | 3 | |
| BHM | YYY | #456346 | #6 Papaya 13681991 | 95% Normal | OK | 4 | 4 | Low Level<br>Cartridge #2-Watermelon in dispenser #456346 at YYY in Birmingham is low |
| | | | #7 Apple 13681996 | 0% Empty | In Transit | 2.7 | 0 | |
| | | | #3 Pineapple 13681993 | 0% Empty | Out of Stock | 2.5 | 0 | |
| | | | #4 Cranberry 13681995 | 24% Low Level | In Transit | 3.6 | 1 | *YESTERDAY*<br>Cartridge Shipped<br>#7 Apple cartridge shipped to Dispenser #456347 at ZZZ in Nashville |
| NSH | ZZZ | #456347 | #5 Mango 13681994 | 78% Normal | OK | 1.1 | 3 | |
| | | | #7 Apple 13681996 | 0% Empty | In Transit | 2.7 | 0 | |
| | | | #8 Coconut 13681997 | 68% Normal | OK | 2.1 | 5 | |

REMOTE BEVERAGE CARTRIDGE SYSTEM

PRIORITY STATEMENT

This application claims priority to, and the full benefit of, U.S. provisional patent application No. 63/338,867 filed on May 5, 2022.

BACKGROUND

The beverage industry today is using a business model which in some ways has been updated only slightly in the past 150 years. The model is two-fold: first, beverage containers (plastic bottles or cans) are delivered to a point-of-sale like a retail store or a dispenser and, second, a fountain dispenser for beverages which are mixed in the dispenser and poured into a cup or other container. Many of the prior art fountain dispensers are managed (cleaned and maintained) manually and physically in the sense that technicians visit regularly to clean them, run diagnostic testing. These prior art dispensers are "dumb" in the sense that they do not "know" who is receiving the beverage for data analytics or communicate user information and diagnostics to a web domain for remote management. The old business model (1) consumes untold energy resources in producing and transmitting single use beverage containers and containers of beverage concentrate, (2) generates huge amounts of waste in the form of discarded single use containers, and (3) fails to provide automatic beverage selection and tracking of data useful to a consumer for many purposes such as nutrition and fitness training.

Most beverages are more than 99% water, and water is heavy. Under the old bottle and can system, the water is added to the concentrate and then it is shipped to the point of sale. Prior art concentrate containers are bulky and require trained technicians to service and replace. Transporting large amounts of heavy beverages is energy intensive, and fails to make use one of the most extensive and costly assets of modern society: a vast system of municipal water piping which moves water in a far more energy efficient way than by trucking. Traditional fountain dispensers use the current municipal piping as a water source, but these dispensers are still managed in an old way: heavy containers of beverage concentrate are manually tracked, shipped, installed and changed in a labor-intensive way without the best use of modern digital technology.

The waste of single-use bottles and cans is only partially addressed by recycling, in that only a small fraction of single use beverage containers are recycled, as suggested by a drive down many highways, or by a walk on a beach. Not only are the energy and waste issues important, but labor is not used efficiently. Current fountain dispensers, in theory, allow for containers which are reusable instead of for single use, but large scale use of reusable containers has not been made because prior art dispensers are not "intelligent" enough to shift consumer behavior significantly.

The smart mobile device and internet connectivity of the last 10-15 years has contributed to the spread of information in many ways, but has largely been ignored by beverage producers. What has been needed is a fundamental rethinking of how beverages are managed and delivered to consumers.

The numerous configurations, features and functions of the system as depicted in the figures and otherwise described here are only exemplary, as these can be combined in ways and embodiments not described specifically herein. That is, the embodiments specifically depicted and described can be re-combined into other embodiments.

ASPECTS OF THE INVENTION

Disclosed is a remote cartridge system 1 for managing concentrate cartridges 6, both for beverages and cleaning, and the dispenser 2 in which they are installed. Each cartridge contains specific cartridge information 8 which is read by a wireless reader and then communicated to a controller 3 of a dispenser allowing remote supervision of maintenance, inventory, cleaning and revision of firmware. The system has a web domain 9 and a mobile app 10 for a smart mobile device which are synchronized, the web domain communicating directly with the controller or indirectly through the smart mobile device.

Figure 1:
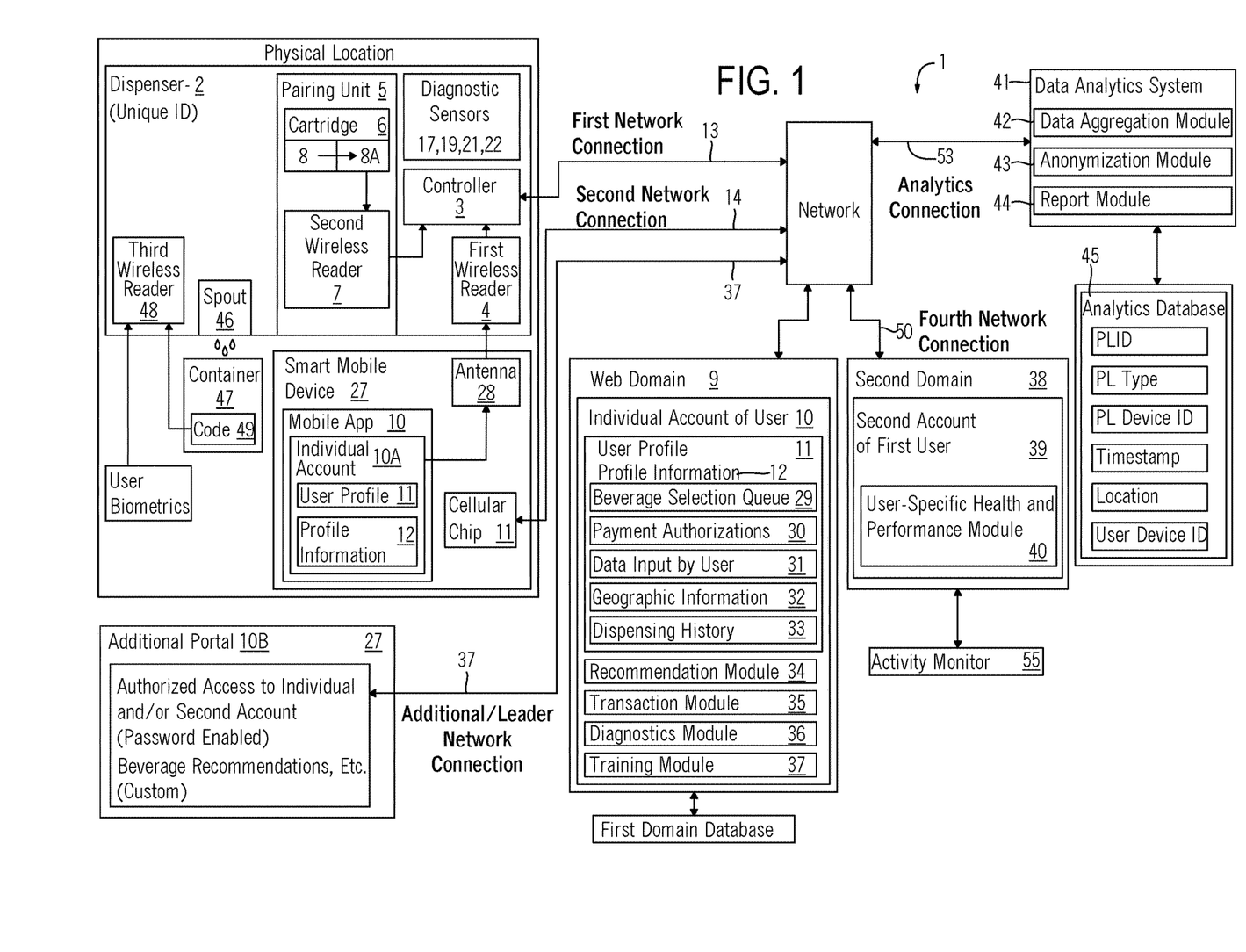
FIG. 1 is a schematic showing the overall structure of one embodiment of the system for individual users comprising first and second domains and a data analytics module hosted separately from the web domain.

In one embodiment shown in FIG. 1, the system 1 comprises a dispenser 2 with a unique dispenser ID and comprising a controller 3, a first wireless reader 4 and at least one pairing unit 5 comprising a cartridge 6 for concentrate, either for a beverage or for cleaning, the cartridge being replaceable and bearing specific cartridge data 8 (e.g., embodied in an NFC tag) shareable by means of a cartridge antenna 8A, a fluid connection between the cartridge and the dispenser, and a second wireless reader 7 on the dispenser configured to read the cartridge antenna and to transmit the specific cartridge data through circuitry 26 to the controller comprising a printed circuit board 3A (FIG. 9), and a web domain 9 and a mobile app 10 downloadable onto a smart mobile device 27 of a user, with the web domain and mobile app synchronized to share information reciprocally. The system 1 further comprises an individual account 10A comprising a user profile ii configured to hold profile information 12, the web domain configured for a first network connection 13 with the controller and a second network connection 14 with the mobile app, and the mobile app configured to communicate with the controller by an antenna 28 of the smart mobile device 27 through the first wireless reader 4. In other embodiments, all the components may exchange data wirelessly. The smart mobile device apart is not a part of the invention, and it only hosts the mobile app. The first, second, additional/leader and fourth network connections 13, 14, 37, 50 are also not part of the invention, but are publicly available communications networks such as the internet and cellular networks.

The first and the second wireless readers are selected from the group consisting of NFC, RFID, Bluetooth and WiFi, and more particularly Bluetooth, mesh IoT network, WiFi: IEEE 802.11 wireless networks (WLAN, WPAN, WWAN) and IEEE 802.15 WPLAN, 3G/4G/LTE cellular communication methods, ZigBee and WPLAN. the smart mobile device antenna and the cartridge antenna are compatible. The controller is configured for wireless communication with the mobile app indirectly by the first and second network connections 14, 37 through the web domain and/or directly with the mobile app through the first wireless reader 4. The first network connection 13 is enabled through a cellular chip and/or a second WiFi chip on the dispenser which relay all data to a cloud computing platform to enable the remote monitoring maintenance, inventory, cleaning and revision of firmware. In another embodiment the WiFi and a cellular chip on the controller, web domain and/or the mobile app are configured to send a trigger for a push notification via the second network connection to the smart mobile device opening the mobile app and/or driving the mobile app.

The user profile 11 holds information for the user interaction with the system. In one aspect the profile information 12 is selected from the group consisting of a unique user ID, the user's age, height, weight, gender, medical condition, fitness goals, planned exercise regimen and timing, beverage choices in a beverage selection queue 29 and payment authorizations 30. This aspect of the profile information is typically data input 31 into the mobile app by the user. In another aspect, in one embodiment the profile information further comprises the user's geographic data 32 selected from the group consisting of location, ambient temperature, relative humidity, altitude and whether an exercise regimen will be in an air-conditioned space. This second aspect can be automatically incorporated into the profile information 12 if the user has activated a setting in his/her smart mobile device for location sharing. The exception to this automatic loading is whether an exercise regimen will be in air conditioning, so that this is data input 31 by the user.

A dispensing session is the period of time starting when the mobile app and the dispenser are in communication due to physical proximity enabling transmission of information to the dispenser from through the first wireless reader and ending when the beverage is dispensed, the dispensing is canceled, the user moves out of wireless range with the dispenser and the like. The ability of the dispenser to dispense a beverage of the user's choice is made quick and easy during a dispensing session because the beverage selection queue 29 is configured to be preset by the user before a transaction; alternatively, the beverage selection queue may be revised in the mobile app by the user during a dispensing session for any reason. The web domain 9, the mobile app 10 and/or the dispenser 2 are further configured, during the session, to match the specific cartridge data 8 for all of the cartridges in the specific dispenser (i.e., where the user is located) with the beverage choices in the beverage selection queue and to generate and send instructions for making a beverage to other components of the dispenser, and to store the transaction in a dispensing history 33. The instructions for making a beverage are made according to the concentrate mix ratio which comprises a proportional value for concentrate volume to beverage volume. The concentrate contents for beverages are selected from the group consisting of electrolytes, caffeine, proteins, amino acids, fats, vitamins, minerals, nutrients, sugars, CBD oil, spirulina, melatonin, flavorings, and the like.

The components of the dispenser involved directly in making a beverage include the controller 3, the beverage cartridges 6, the pump 24, and circuitry 26 connecting them.

The specific cartridge data 8 is selected from the group consisting of a beginning volume, a concentrate mix ratio, a cleaning mix ratio, a unique cartridge ID, an ID for contents, expiration date, fill date and lot number.

An important aspect of the invention's ability to manage cartridges remotely is tracking the volume in a cartridge over time. The methods for doing so may vary. In one embodiment, the controller 3 and/or a transaction module 35 in the web domain 9 and/or the mobile app 10 are configured to subtract from the beginning volume a concentrate dose volume as dispensed for each beverage and to calculate a running total of remaining volume of each of the cartridges. This method is strictly mathematical and does not rely on any physical sensor. Based on the running total of remaining volume in each cartridge, the transaction module is further configured to send and/or display notices for replacement cartridges to a system administrator, a cartridge fulfillment system and/or an inventory tracking system.

The concentrate dose volume as dispensed from the spout 46 to the user's container 47, in one embodiment, is determined by instructions in the controller interacting with the concentration ratio contained in the specific cartridge data 8. In just one example of how the system can mix the user's beverage, if the beverage choice is for a 24 ounce watermelon flavored beverage with caffeine, then the controller will apply a concentration ratio of 1:75 for the watermelon flavoring found in the specific cartridge data if the watermelon cartridge, and a concentration ratio of 1:75 for the caffeine also found in the specific cartridge data on the caffeine cartridge. This will produce a watermelon flavoring dose of 0.32 ounce and a caffeine dose of 0.32 ounce, all to be mixed with approximately 24 ounces of water. The above is only one example of mixing a beverage, as the concentration ratio can be changed readily by modifying the specific cartridge data for a particular cartridge. And, importantly, the concentrate dose volume of 0.32 ounce will be deducted from the running total of remaining volume in each of the watermelon and caffeine concentrate cartridges, and so on.

In other embodiments, at least one physical sensor is placed on, in or near the cartridge to sense how much volume has been dispensed or remains in a cartridge. The physical sensors are selected from the group consisting of a piston sensor, a flow meter, a load cell, a peristaltic pump, a squeeze film pressure sensor, a spring loaded sensor, an optical sensor, air pressure and the like. In another embodiment there is a read/write function on the system to actually write the updated serving size to each cartridge chip (EEPROM or similar) after each cycle.

The profile information comprises selection of payment authorizations 30 comprising a metered rate or a subscription, and/or the payment authorizations can be located in the transaction module 35.

In one embodiment, a cartridge in at least one of the pairing units 5 is a cleaning cartridge, and the controller and/or the transaction module is configured to instruct the cleaning cartridge to release cleaner to other components of the dispenser. The concentration ratio of the cleaner contained in the specific cartridge data is mixed with water in a manner similar to that as described herein in the example of the watermelon caffeine beverage.

The fluid connection between the cartridges and the dispenser (see FIG. 7), in one embodiment, comprises dosing plumbing tubes using a threaded, push-to-connect check valve. This fitting threads into a mechanical cartridge receiver on the dispenser, which is a custom designed component that allows the cartridge endcap to thread into a ¼ turn mechanism to hold it in place securely. It also provides a surface that pushes the cartridge endcap plunger up into a 'dose' position when the cartridge is fully inserted.

In one embodiment the web domain and/or the mobile app further comprise a recommendation module 34 configured to generate, from the profile information 12 and the dispensing history 33, a recommended beverage intake (RBI) as the instructions for making a beverage. In another embodiment the system is further configured for an additional/leader network connection 37 between the individual account 10A and an additional portal to the user's individual account, the additional portal configured to enable a second user (e.g., a trainer or health care professional) to specify the RBI as mandatory or suggested, to make a custom recommendation for the user or to perform data analysis. The system is further configured for incorporating user-specific health and performance information 40 of the user into the RBI, wherein the user-specific health and performance information is collected by user input 31, an activity monitor and/or other sensor and is found within (a) the profile information 12, (b) a training module 37 in the web domain and/or (c) a second web domain 38 with a fourth network connection 50 to and/or from the second web domain, wherein the user maintains a second account 39 comprising the user-specific health and performance information. The user-specific health and performance information is selected from the group consisting of length of exercise session, current or exercise session respiratory rate, resting heart rate, heart rate variability, quantity of sleep during a prior period, sleep performance during a prior period, volatile organic compounds from exhalation, biochemical levels in blood, interstitial fluid or cerebrospinal fluid, electrodermal activity, VO2 max, stress, caloric burn, training effect, power curve, functional threshold power, lactate level, lactate threshold, strain and recovery.

In additional embodiments, the recommendation module 34 formulates the RBI by factoring in the user-specific health and performance information, and by factoring in output from a data analytics system 41 (incorporating its data aggregation module 42, anonymization module 43, and the output may be derived from sentiment analysis, third party research, and aggregated user information. The recommendation module 34 may contain instructions for different weightings of the above information to achieve different health and training goals.

The dispenser 2 herein in one embodiment is a stand alone device, and in another embodiment is configured to be housed inside another device selected from the group consisting of a refrigerator, water filtration system and water dispenser.

In another embodiment, a third wireless reader 48 reads information of the user or a code 49 (e.g., a QR code) and authorizes a transaction. For example, the third wireless reader may be a reader of biometric information using fingerprint, facial, voice or iris recognition. Once the user is identified, the user may be recognized. In another example, the user's account may be recognized by a QR or barcode tag on the user's container in which example the third wireless reader is a QR or barcode scanner. In such a beverage dispensing session, the web domain 9 authorizes the user's transaction which is present by the user for a beverage choice in the beverage selection queue 29.

The system 1 can also incorporate user-specific health and performance information 40 from a sensor configured to connect with the mobile app configured to connect with the mobile app configured to connect with the mobile app configured to connect with the mobile app (a) implanted in the member's body and communicates transcutaneously with an externally mounted device and the mobile app or (b) implanted in or affixed to the member's body and communicates percutaneously with an externally mounted device configured to connect with the mobile app on a smart mobile device. Alternatively, the sensor is configured to communicate wirelessly with an activity monitor capable of being worn by the user. Or, in another embodiment, an activity monitor may connect wirelessly with the mobile app.

The remote monitoring and maintenance is enabled in various embodiments wherein the dispenser further comprises at least one of each of a leak detector 21, a flow meter 19, a temperature sensor 22, and a water pressure sensor 17 communicating through the controller to a diagnostic module 36 in the web domain 9.

Figure 7:
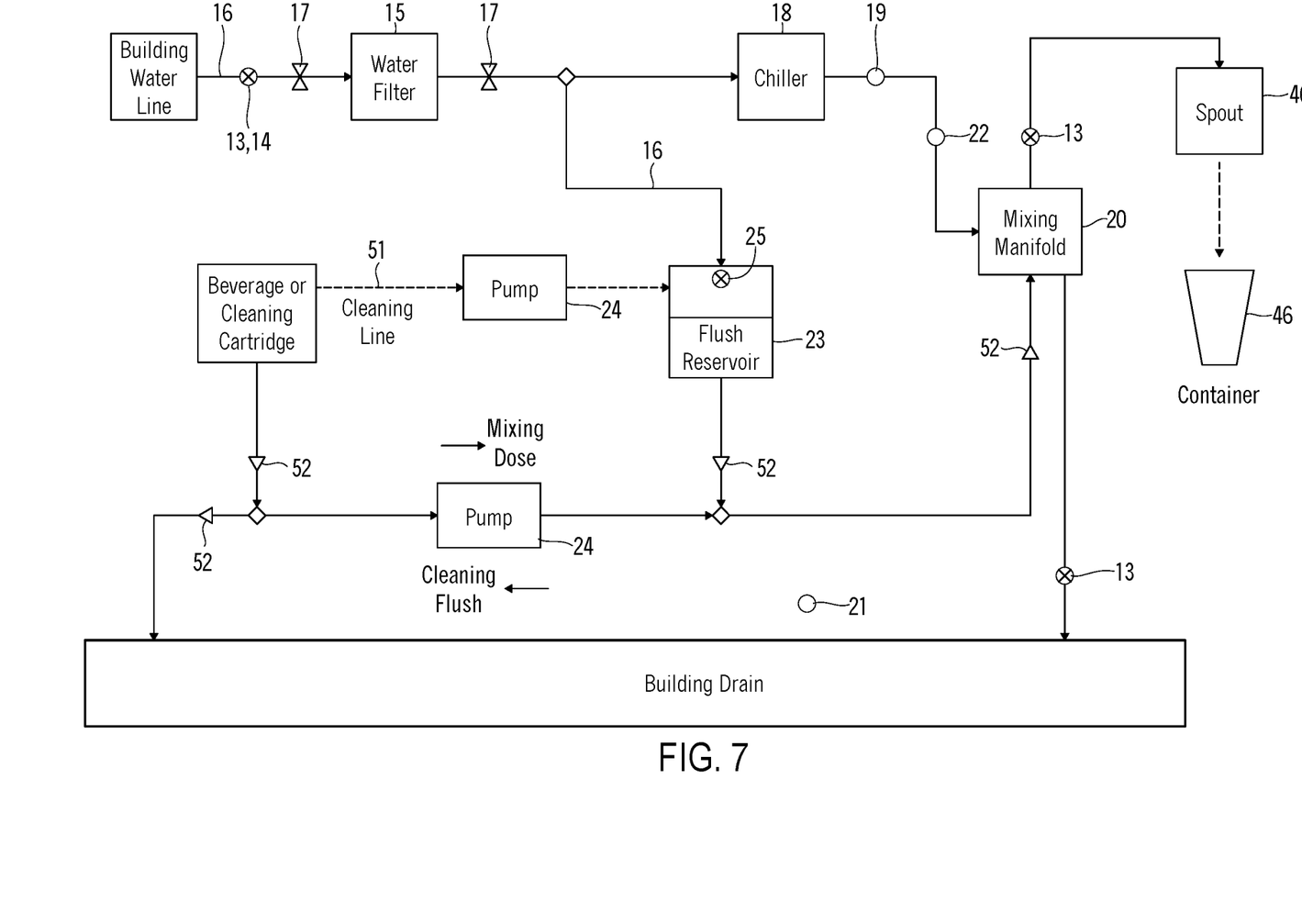
FIG. 7 is a schematic of the fluid aspects of one embodiment of the dispenser herein.

FIG. 7 is a schematic showing a flow diagram of one embodiment of the dispenser showing components for pumping and mixing a beverage or sending a cleaning dose from concentrate, as well as sensors in one embodiment of the dispenser. The building water line is connected to the water line 16 in the dispenser 2 which passes through a solenoid 13 or a ball valve 14 and continues to a water filter 15. Over time the water filter will clog at different rates depending on the solids in the municipal water, and it is important to monitor the actual state of the water filter so the system 1 can generate a recommendation through the controller to the system administrator that the water filter be changed. As solids in the municipal water accumulate in the water filter, the pressure in the dispenser water line 16 will become greater before passing into the water filter, and rate of the filtered water will slow In one embodiment, then, a first water pressure sensor 17 is placed into the tubing of the dispenser water line prior to and a second water pressure sensor 17 after the water filter. Each water pressure sensor is electrically connected with the controller which measures the difference between the two pressure sensors automatically, and the controller relays this information to the diagnostics module 36 As the differential between these water pressure sensors grows, or the pressure in the second water pressure sensor, the diagnostics module will notify the system administrator or other responsible person to replace the water filter. After the filtered water passes through a chiller 18, a flow meter 19 in the water line 16 reports the actual water flow to the controller as the filtered and chilled water passes into the mixing manifold 20 to report flow to the controller in order to (1) adjust the dosing if necessary, and (2) to report through the controller 3 to the diagnostic module 36. A temperature sensor 22 in the water line 16 between the chiller 18 and the mixing manifold reports the chilled water temperature to the controller and then to the web domain 9, in order to adjust the chiller or to be notified about a possible need to replace the chiller. A leak detector 21 on or near the bottom of the dispenser interior close to the dispenser drain to the building also reports the presence of standing liquid to the controller which is indicative of a leak in the dispenser, allowing the controller to send a signal for automatic shutoff to the inlet solenoid valve. A float valve 25 in the flush reservoir 23 closes and cuts-off the municipal pressure once the reservoir is full and the float is in the "up" position. From the flush reservoir the filtered water reaches the pump 24 which pumps in opposite directions. One direction pumps concentrate to the mixing manifold 20 for dispensing a beverage and the other direction pumps filtered water to clean the pump and then to a drain. As shown by the arrows showing opposite directional flows for dosing versus flushing, a pump 24 with reversible flow allows the flush reservoir to release water for passing through the pump to flush the pump and clean it of beverage concentrate. Other pump configurations can comprise a pump selected from the group consisting of a diaphragm pump an impeller pump. These pumps have different capabilities than a peristaltic pump, so the configuration of the fluid flow in the embodiment as shown in FIG. 7 could vary. Peristaltic pumps are reversible and can act as a check valve, which allows fluid flow in only one direction. A cleaning cartridge 6 is connected to a cleaning line 51 which connects into the flush reservoir, rather than into the mixing manifold 20. What is shown in FIG. 7 is only one cartridge 6 with a pump dedicated to that single cartridge although there are multiple cartridges in the dispenser, each cartridge paired with a pump 24. That is, in one embodiment of a dispenser with seven beverage concentrate cartridges and one cleaning cartridge, there will be eight pumps, each dedicated to one cartridge. Check valves 52 allow water to flow in only one direction. A cleaning cartridge 6 routes cleaner through a cleaning line 51 differently than the concentrate from a beverage cartridge. The cleaning line goes directly to the flush reservoir 23 which is connected to all the pumps 24 for all the beverage concentrate cartridges. In FIG. 7, the cleaning cartridge is shown separately only to demonstrate that its output is to the flush reservoir.

The cartridge 6 in at least one of the pairing units 5 is a cleaning cartridge, and the controller and/or the transaction module is configured to instruct the cleaning cartridge to release cleaner to other components of the dispenser. The cleaning cartridge 6 (containing a concentrated, food grade cleaning/de-scaling agent, such as food-grade vinegar or citric acid) is inserted into position within the dispenser. The cleaning cartridge operates in the same manner as the other cartridges which are for beverages. That is, associated with each pairing unit 5 is a mechanical receiver assembly (not shown), an NFC reader, check valve (2) and tee), however the cleaning cartridge is plumbed into the flush reservoir 23 rather than into the mixing manifold 20. A periodic cleaning cycle is programmed to run at an ideal time, for example at 2:00 AM when the location is closed and no one is present. By means provided by the dedicated pump, the cleaning cartridge sends the cleaning concentrate from the cartridge into the flush reservoir while simultaneously the other pumps run in reverse, each drawing the cleaning solution/filtered water mix from the flush reservoir 23. The cleaning fluid leaves the flush reservoir at the flow rate of the beverage dosing pumps 24, and enters the flush reservoir at the same rate via a combination of the cleaning pump 24 and the fresh water added as the reservoir level drops and the float valve drops/opens. The cleaning solution then run through all the beverage pumps and their associated plumbing lines, and then to the building drain. At the end of this cycle, all beverage dosing pumps run forward (opposite direction as before) to prime the lines with concentrate while pushing the remaining cleaning solution out of the dispensing spout. This cycle allows all of the plumbing lines and components (save the small line between the cartridge inlet and a, a diamond shape (below the beverage cartridge in FIG. 7) to be cleaned.

Figure 8:
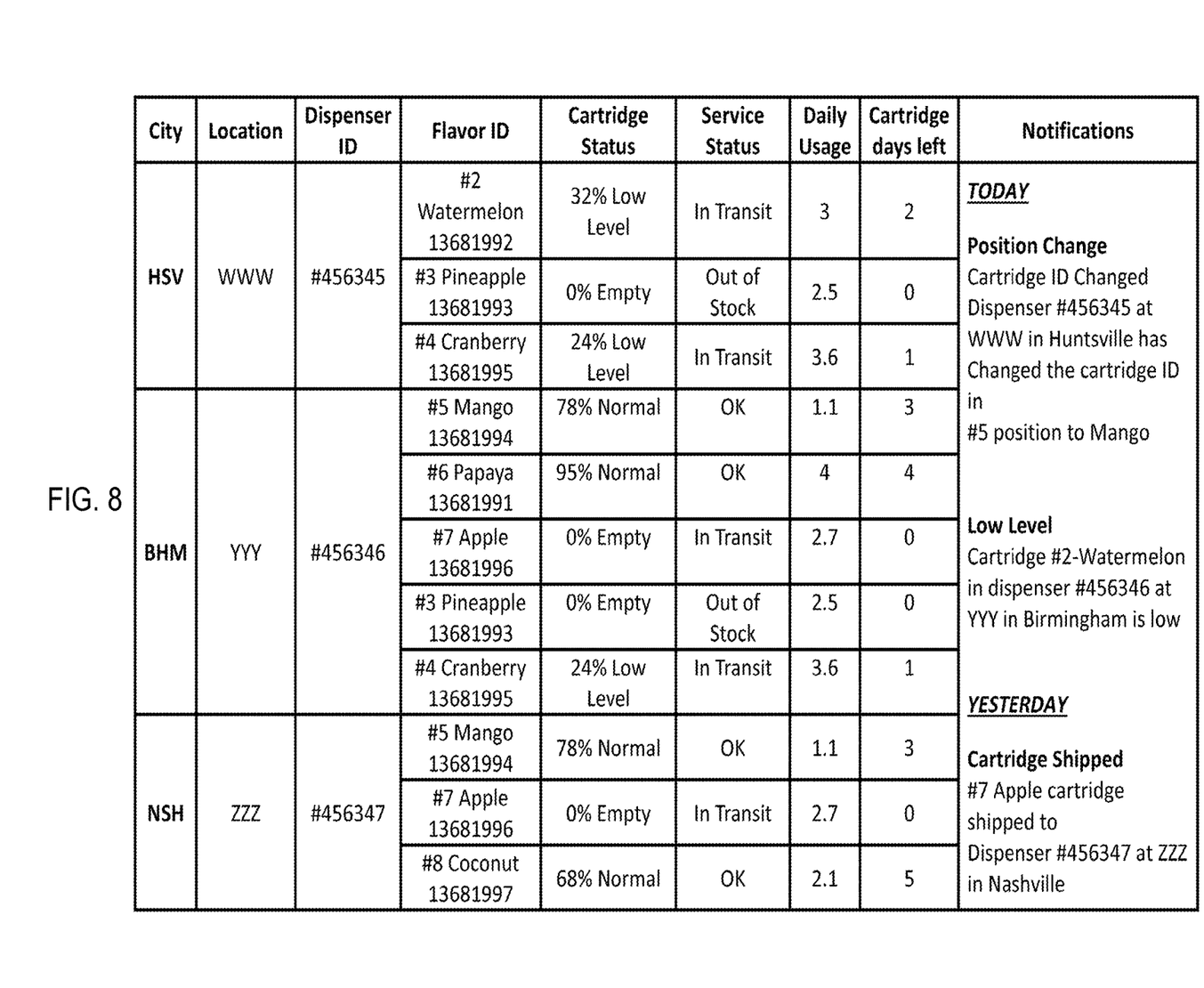
FIG. 8 is one embodiment of a remote cartridge dashboard as described in this application.

The controller collects information collected from the dispenser including, without limitation, the running total of the remaining volume in the cartridges, and readings from the sensors, and then relays it to the web domain 9. The controller, in one embodiment, calculates a value for the remaining volume in the concentrate (e.g., 80% or 100 beverage doses remaining) and transmits this value to the web domain. In another embodiment, the dispenser transmits only the raw data and the calculation of this value is made in the web domain, and the raw data may be stored in a database in the web domain or a database accessed separately. As calculated and stored, this information may be displayed in a dashboard as shown in in FIG. 8, an abbreviated depiction in the Flavor ID column showing only a portion of the cartridges in a typical dispenser. In one embodiment, data about each cartridge reported from the controller is as follows:
1. City
2. Location (e.g. Name of facility)
3. Dispenser ID
4. Flavor ID
5. Cartridge status (e.g. 30%, low; incorrect cartridge installed)
6. Service Status (e.g. cartridge in transit)
7. Daily Usage (e.g. amount of drinks/oz/gallons used per day)
8. Cartridge days left (e.g. 5 days left/20 beverages left/5 oz. left)
9. Estimated Time of Arrival of Cartridge
10. Notifications The combination of the data collected from the dispenser and the notification to the web domain 9 then generates notifications for the system administrator or automatic systems for cartridge fulfillment. These notifications greatly reduce the amount of regular service calls for maintenance, and allows replacement cartridges to be shipped to the physical location where employees or the owner of the business or home can replace the empty cartridge.

Another version of the dispenser fluid mechanism is described in international patent application PCT/US20/61049 (the '049 application), which is incorporated herein in its entirety, and which can dispenser can be used in various embodiments of the present system 1. The sensors described in the instant application can be applied to the embodiments in the '049 application, and additional architectures for the fluid mechanism of the dispenser for the present system 1 are possible.

Figure 9:
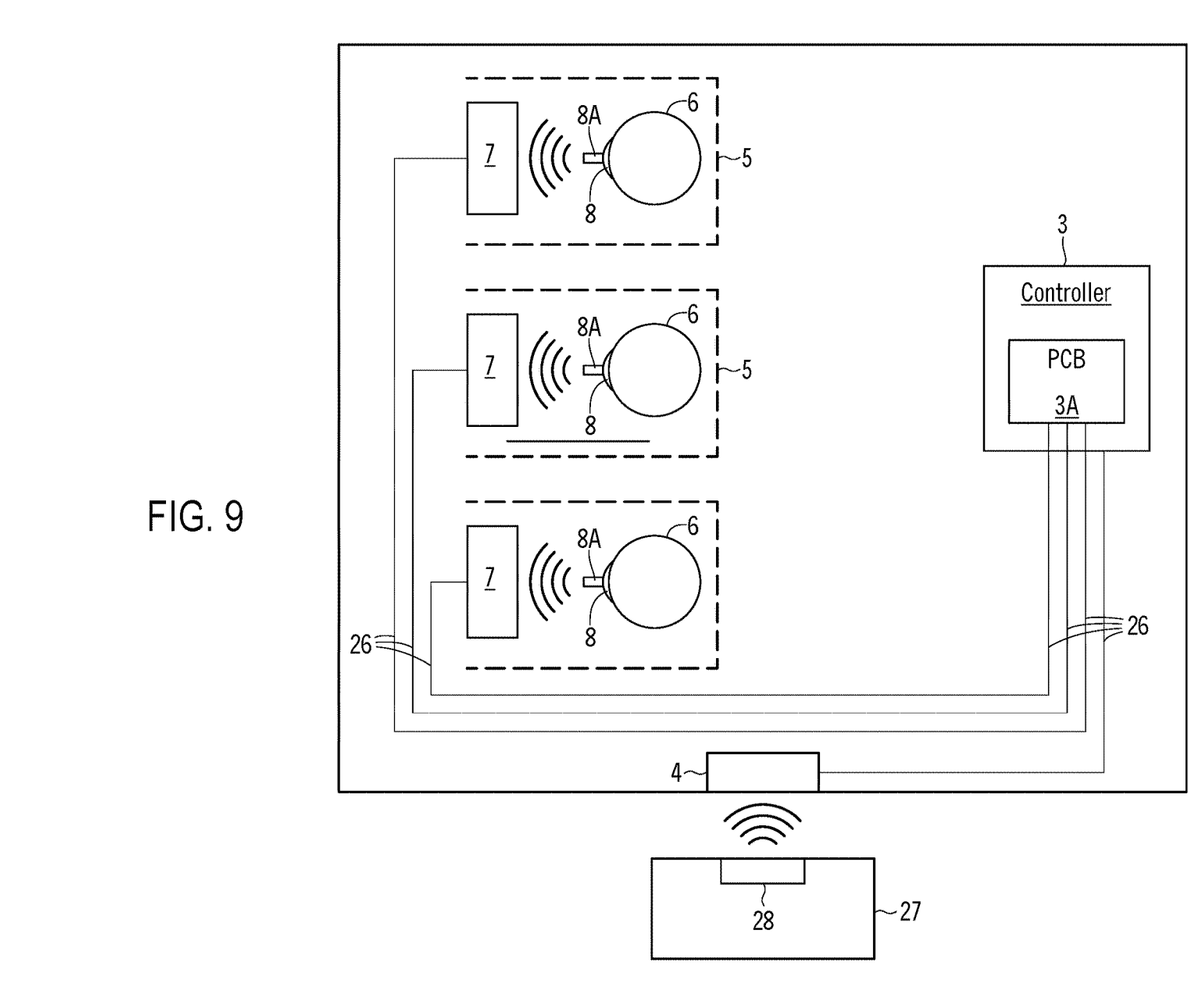
FIG. 9 is a schematic of one embodiment of the pairing unit of the cartridge with a tag containing specific cartridge information and a second wireless reader.

FIG. 9 is a schematic of one embodiment of the dispenser 2 with three pairing units 5 (any number is possible) in which the cartridge 6 bearing specific cartridge information 8 is transmitted by an antenna 8A to the second wireless reader 7. The specific cartridge information is transmitted by circuitry 26 to a printed circuit board 3A or other processor in the controller 3. The first wireless reader 4 can send and receive information to and from the smart mobile device 27 through the latter's antenna 28.

The first network connection 13 allows the web domain 9 to remote delivery of firmware updates to the controller in a dispenser directly, or indirectly through a smart mobile device when the dispenser is not connected.

Figure 2:
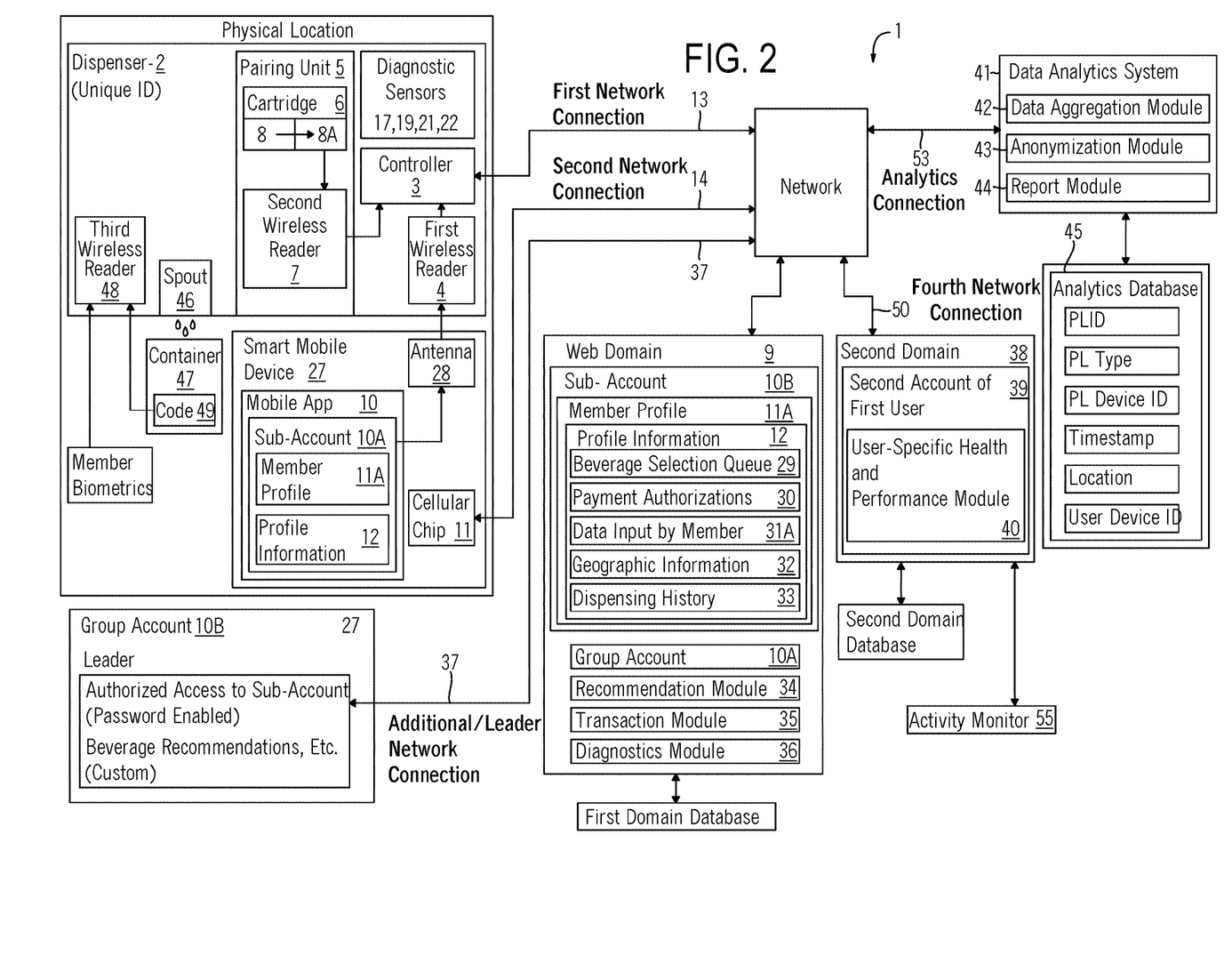
FIG. 2 is a schematic showing the overall structure of one embodiment of the system for a group account and sub-accounts comprising first and second domains and a data analytics module hosted separately from the web domain. A leader has a group account and members have sub-accounts.

As shown in FIG. 2, another embodiment of the remote beverage cartridge system 1 uses the same pairing unit 5 but, instead of individual accounts, employs group 10B and sub-accounts 10C, respectively, for a group leader and its members. This embodiment is similar to the embodiment for individual accounts in that it comprises at least one dispenser 2 with a unique dispenser ID and comprising a controller 3, a first wireless reader 4 and at least one pairing unit 5 comprising a cartridge 6 for concentrate, the cartridge being replaceable and bearing specific cartridge data 8 shareable through a cartridge antenna 8A, a fluid connection between the cartridge and the dispenser, and a second wireless reader 7 on the dispenser configured to read the cartridge antenna 8A and to transmit the specific cartridge data 8 to the controller 3. The group embodiment differs though in that the web domain 9 and a mobile app 9B for downloadable onto smart mobile devices 27 of a leader and members of a group, the web domain and the mobile app sharing information reciprocally and comprising a group account 10B controlled by the leader and a sub-account 10C for each of the members of the group, the group account comprising tools for managing and communicating with the sub-accounts configured to hold profile information 12 about each of the members, said web domain configured for a first network connection 13 with the controller 3 and a second network connection 14 with the mobile app 9A on the leader's and each of the members' smart mobile devices, and the mobile app configured to communicate with the controller by an antenna 28 of the smart mobile device 27 through the first wireless reader 4.

The profile information 12 is selected from the group consisting of a unique member ID, the member's age, height, weight, gender, medical condition, fitness goals, planned exercise regimen and timing, beverage choices in a beverage selection queue 29 and payment authorizations 30.

The beverage selection queue 29 is configured to be preset before a transaction or revised during a dispensing session.

The web domain, the mobile app and/or the dispenser are further configured to match the specific cartridge data for all of the cartridges with the beverage choices in the beverage selection queue and to generate and send instructions for making a beverage to other components of the dispenser, and to store the transaction in a dispensing history for each of the members. The components of the dispenser involved directly in making a beverage include the controller 3, the beverage cartridges 6, the pump 24, and circuitry 26 connecting them.

The specific cartridge data 8 is selected from the group consisting of a beginning volume, a concentrate mix ratio, a cleaning mix ratio, a unique cartridge ID, an ID for contents, expiration date, fill date and lot number.

The controller 3 and/or a transaction module 35 adapted for each of the members in the web domain and/or the mobile app are configured to subtract from the beginning volume a concentrate dose volume dispensed for each beverage and to calculate a running total of remaining volume of each of the cartridges.

The cartridge 6 in at least one of the pairing units 5 is a cleaning cartridge, and the controller and/or the transaction module is configured to instruct the cleaning cartridge to release cleaner to other components of the dispenser. Further details about cleaning are described elsewhere herein.

The controller is configured for wireless communication with the mobile app indirectly by the first and second network connections 13, 14 through the web domain and/or directly with the mobile app through the first wireless reader 4.

The transaction module is further configured to send and/or display notices for replacement cartridges to a system administrator, a cartridge fulfillment system and/or an inventory tracking system.

The first and the second wireless readers 4, 7 are selected from the group consisting of NFC, RFID, Bluetooth and WiFi, and the smart mobile device antenna and the cartridge antenna are compatible.

The web domain and/or the mobile app further comprise a recommendation module 34 configured to generate, from the profile information 12 and the dispensing history, a recommended beverage intake (RBI) as the instructions for making beverage.

The profile information further comprises the user's member's geographic information 32 selected from the group consisting of location, ambient temperature, relative humidity, altitude and whether an exercise session will be in an air-conditioned space.

The tools for managing and communicating with the sub-accounts 10C comprise specifying the RBI as mandatory or suggested, making a custom recommendation for the members or performing data analysis.

The is further configured for incorporating member-specific health and performance information of the user into the RBI, wherein the member-specific health and performance information is collected by input, an activity monitor and/or other sensor and is found within (a) the user profile ii, (b) a training module 37 in the web domain 9 and/or, (c) a second web domain 38 with an external network connection to and/or from the second web domain, wherein the member maintains a second account 39 comprising the member-specific health and performance information. The second web domain and the second account are not part of the invention herein.

The member-specific health and performance information is selected from the group consisting of length of exercise session, current or exercise session respiratory rate, resting heart rate, heart rate variability, quantity of sleep during a prior period, sleep performance during a prior period, volatile organic compounds from exhalation, biochemical levels in blood, interstitial fluid or cerebrospinal fluid, electrodermal activity, VO2 max, stress, caloric burn, training effect, power curve, functional threshold power, lactate level, lactate threshold, strain and recovery.

The analytics tools described elsewhere in this specification are equally applicable to this embodiment of the system 1 with group 10B and sub-accounts 10C.

Figure 4:
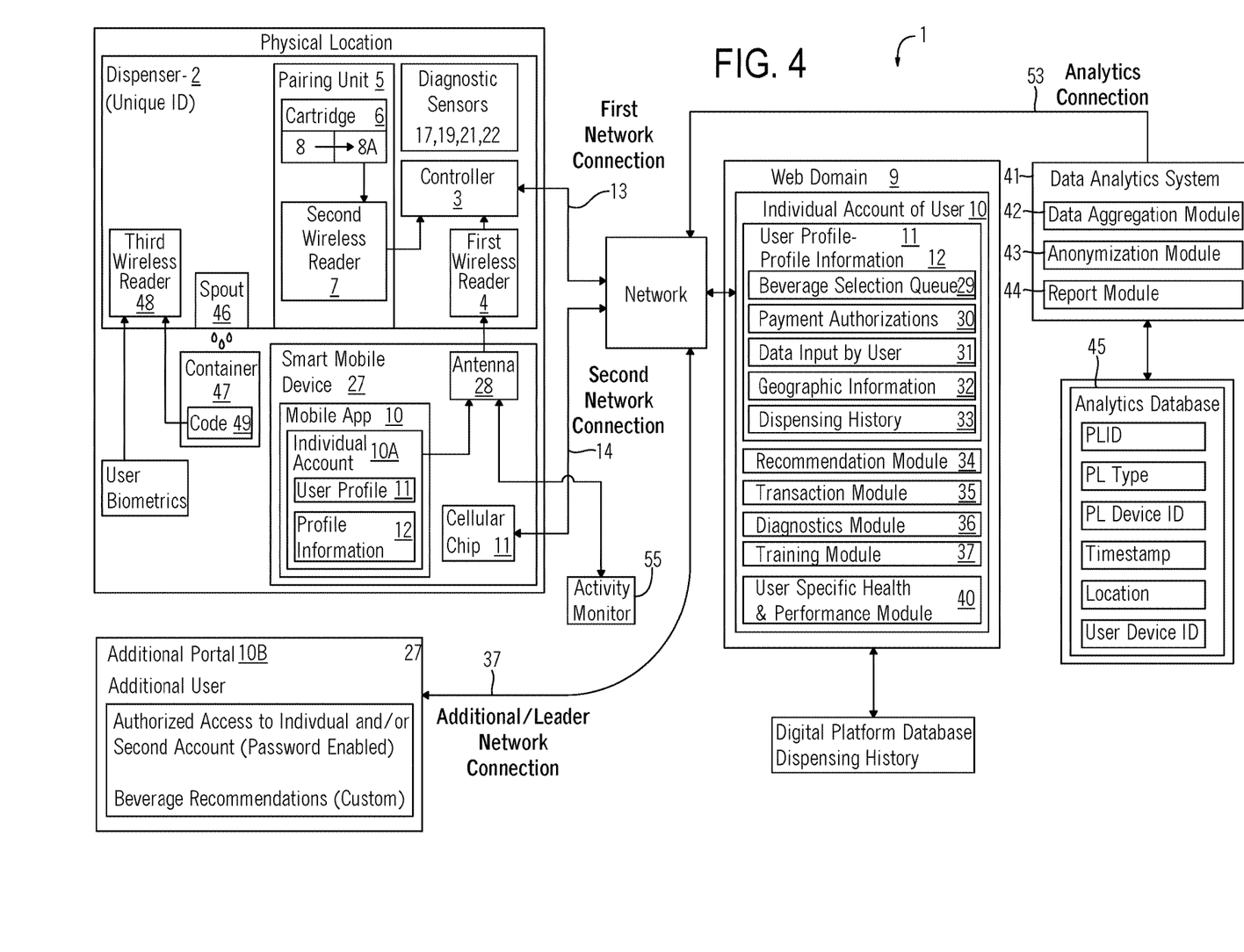
FIG. 4 is a schematic showing the overall structure of another embodiment of the system for individual users without a connection to a second domain.

FIG. 4 is a schematic showing the overall structure of another embodiment of the system for individual users without a connection to a second domain.

Figure 3:
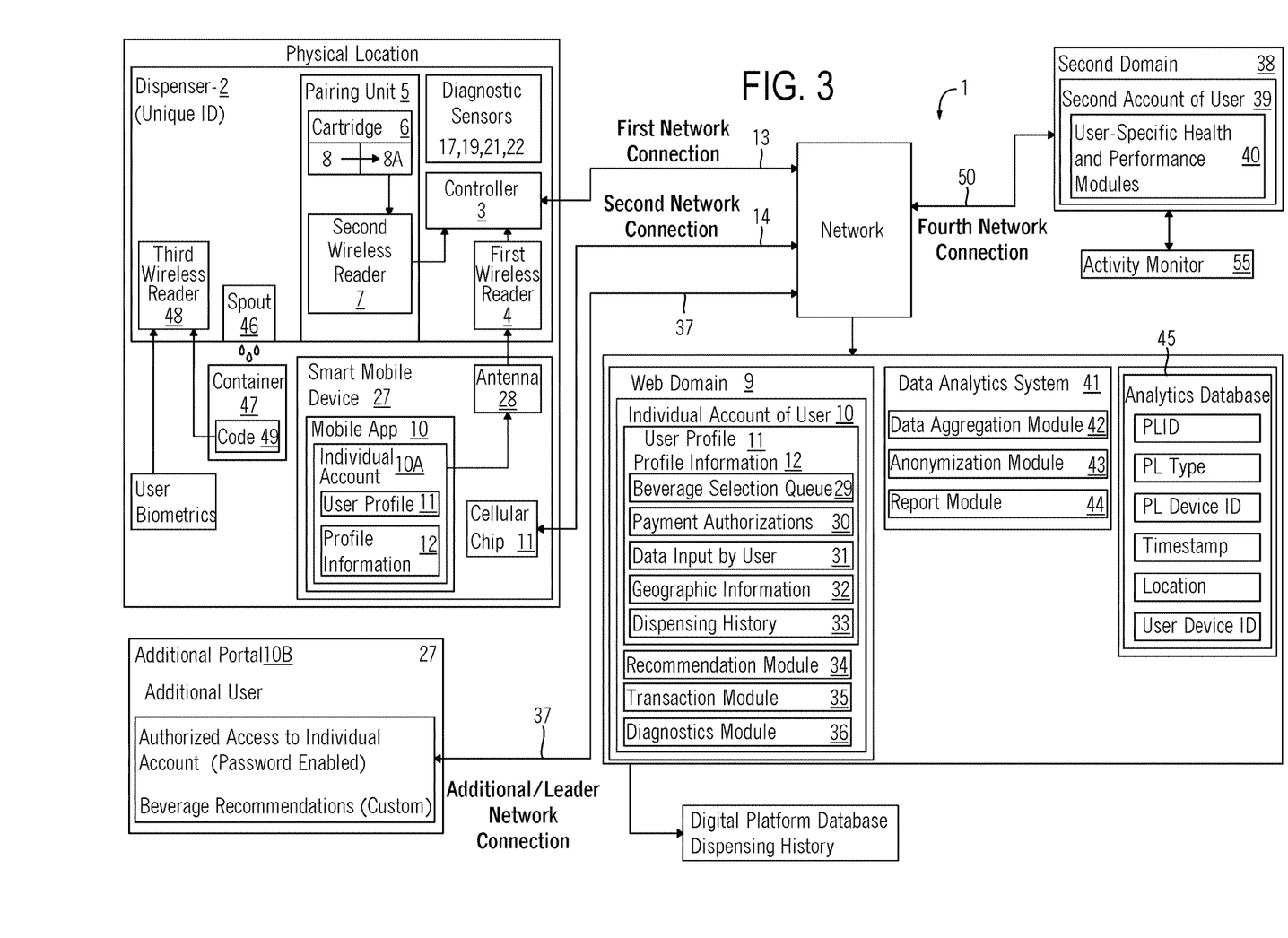
FIG. 3 is a schematic showing the overall structure of an embodiment of the system with the analytics system and database within a single web domain.
Figure 5:
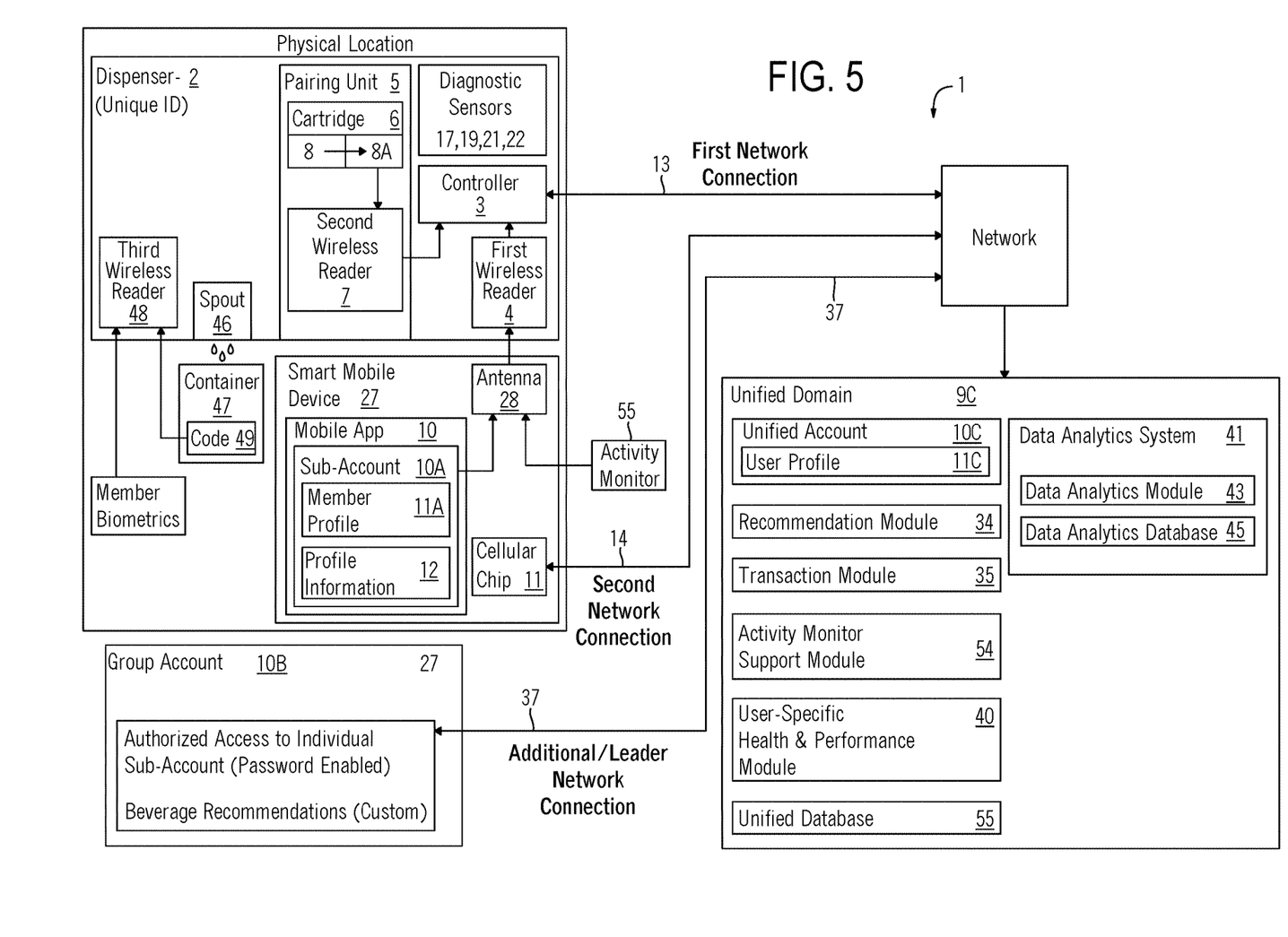
FIG. 5 is a schematic of an embodiment of the system with a unified domain for individual users comprising the first and second domains of FIGS. 1, 2 and 3.

FIG. 5 is a schematic of an embodiment of the system with a unified domain for individual users comprising the first and second domains of FIGS. 1, 2 and 3.

Figure 6:
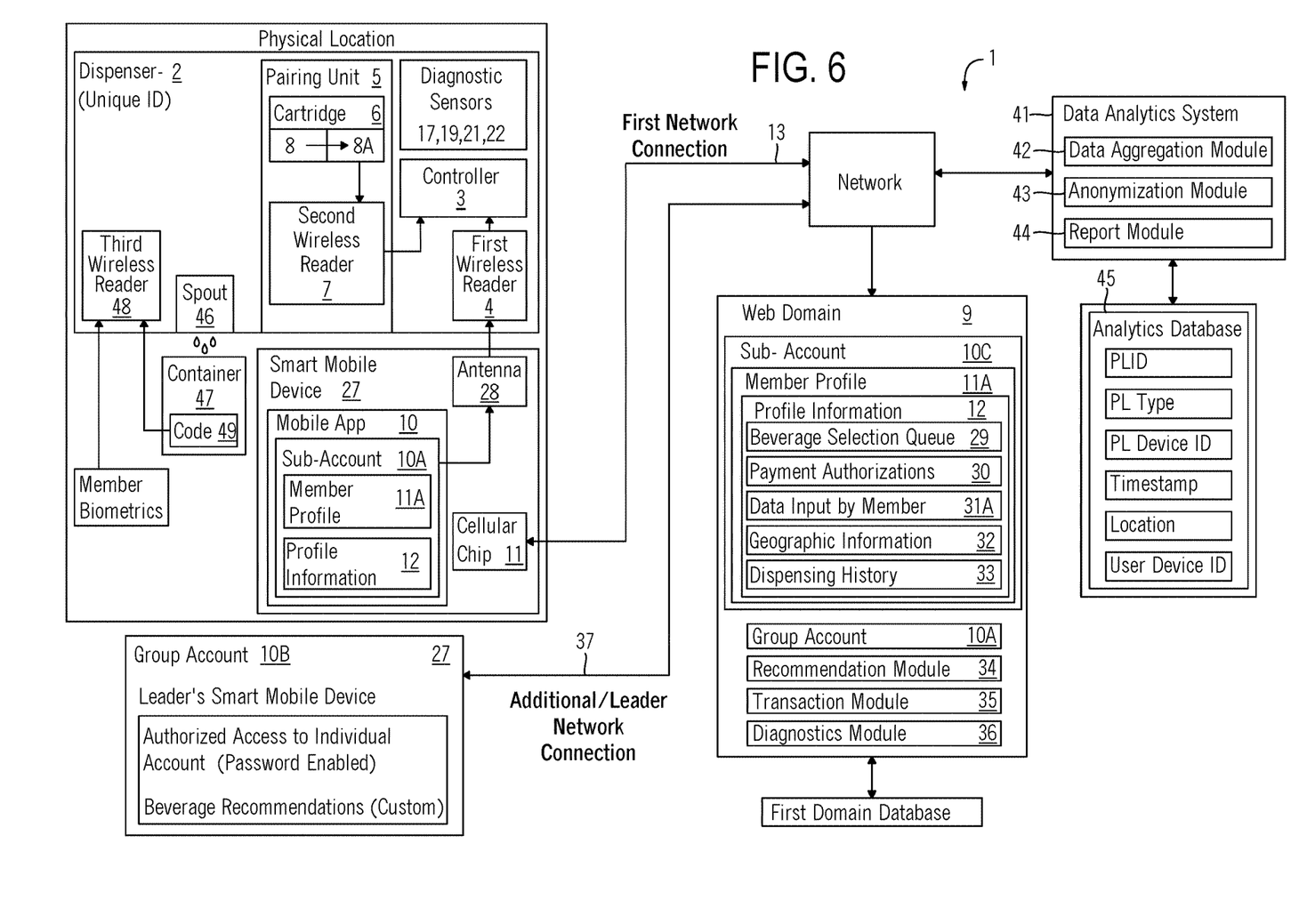
FIG. 6 is a schematic of the system in which the dispenser communicates with the web domain indirectly through a smart mobile device.

Another leader-and-member embodiment of the remote beverage cartridge system 1 is for remote management of cartridges in a beverage dispenser for a leader and members of a group. FIG. 6 is a schematic of this embodiment of the system 1 in which the dispenser has no direct connection to the web domain but communicates with the web domain indirectly only through a smart mobile device.

In this embodiment, however, the dispenser is connected to the web domain 9 indirectly through the smart phone of the mobile app 10 of the group or the members of the group. As in other embodiments, the dispenser 2 comprises a first wireless reader 4 and a controller 3, and at least one pairing unit 5 comprising a cartridge 6 for concentrate, the cartridge being replaceable and bearing specific cartridge data 8 shareable through a cartridge antenna 8A, a fluid connection between the cartridge and the dispenser, and a second wireless reader 7 configured to read the cartridge antenna 8A and to transmit the specific cartridge data 8 to the controller, and a web domain 9 and a mobile app 10 downloadable onto a smart mobile device 27 by a leader and members of a group, the web domain and the mobile app sharing information reciprocally by a first network connection 13, the mobile app comprising a group account 10B controlled by the leader and a sub-account 10C for each of the members of the group, the group account 10B comprising tools for managing and communicating with each of the sub-accounts having a member profile 11A configured to hold profile information 12 about one of the members, and the mobile app being shareable by an antenna 28 of the smart mobile device 27 with the controller 3.

The profile information 12 is selected from the group consisting of a unique member ID, the member's age, height, weight, gender, medical condition, fitness goals, planned exercise regimen and timing, beverage choices in a beverage selection queue and payment authorizations.

The beverage selection queue 29 is configured to be preset before a transaction or revised by the user during a dispensing session.

The web domain 9, the mobile app 10 and/or the dispenser 2 are further configured to match the specific cartridge data for all of the cartridges with the beverage choices in the beverage selection queue 29 and to generate and send instructions for making a beverage to other components of the dispenser, and to store the transaction in a dispensing history 33 for each of the members.

The specific cartridge data 8 is selected from the group consisting of a beginning volume, a concentrate mix ratio, a cleaning mix ratio, a unique cartridge ID, an ID for contents, expiration date, fill date and lot number.

The controller 3 and/or the transaction module 35 adapted for each of the members in the web domain and/or the mobile app are configured to subtract from the beginning volume a concentrate dose volume dispensed for each beverage and to calculate a running total of remaining volume of each of the cartridges.

The cartridge 6 in at least one of the pairing units 5 is a cleaning cartridge, and the controller and/or the transaction module is configured to instruct the cleaning cartridge to release cleaner to other components of the dispenser.

The transaction module is further configured to send and/or display notices for replacement cartridges to a system administrator, a cartridge fulfillment system and/or an inventory tracking system.

The first and the second wireless readers 4, 7 re selected from the group consisting of NFC, RFID, Bluetooth and WiFi, and the smart mobile device antenna 28 and the cartridge antenna 8A are compatible.

The web domain and/or the mobile app further comprise a recommendation module 34 configured to generate, from the profile information 12 and the dispensing history 33, a recommended beverage intake (RBI) as the instructions for making a beverage.

The profile information further comprises the user's member's geographic information 32 selected from the group consisting of location, ambient temperature, relative humidity, altitude and whether an exercise session will be in an air-conditioned space.

The tools for the leader in the group account 10B for managing and communicating with the sub-accounts 10C comprise specifying the RBI as mandatory or suggested, making a custom recommendation for the members or performing data analysis.

The system 1 of this embodiment is configured for incorporating member-specific health and performance information of the user into the RBI, wherein the member-specific health and performance information is collected by member or leader input, an activity monitor and/or other sensor and is found within: the member profile 11A, a training module 37 in the web domain and/or a second web domain 38 with an external network connection to and/or from the second web domain, wherein the member maintains a second account 39 comprising the member-specific health and performance information.

The member-specific health and performance information is selected from the group consisting of length of exercise session, current or exercise session respiratory rate, resting heart rate, heart rate variability, quantity of sleep during a prior period, sleep performance during a prior period, volatile organic compounds from exhalation, biochemical levels in blood, interstitial fluid or cerebrospinal fluid, electrodermal activity, VO2 max, stress, caloric burn, training effect, power curve, functional threshold power, lactate level, lactate threshold, strain and recovery.

The analytics tools described elsewhere in this specification are equally applicable to this embodiment of the system 1 with group and sub-accounts.

In another embodiment the system 1 further comprises a touch screen to display available cartridges to a member or other user during a beverage session, and to enable a member or user to choose a beverage.

All of the embodiments of the remote beverage cartridge system 1 herein are able to be connected to a data analytics system 41 comprising an aggregation module 42, an anonymization module 43 and a report module 44. The data analytics system and an analytics database 45 are linked to the web domain 9, i.e., through a commercially available back-end system such as that provided for example by AWS or Microsoft (as shown in FIG. 2), or through the operator's own system.

The analytics system 41 and analytics database 45 are depicted in FIGS. 1, 2 and 4 as being hosted, outside the web domain 9 of the system 1, by a third party provider, and in these embodiments the analytics system 41 communicates with the web domain over publicly available communications networks. FIG. 3 is a schematic showing the overall structure of an embodiment of the system with the analytics system and database within a single web domain. FIG. 5 is a schematic showing the web domain 9 containing the user-specific health and performance module 40, described elsewhere in this application as residing in a second web domain. That is, in the unified domain embodiment of FIG. 5, the user-specific health and performance information is collected into the unified domain 9C in the first instance from, e.g., an activity monitor or other sources like electronic health records generated by health care providers and uploaded into the unified domain through an API.

The data analytics system 41 is configured to collect numerous categories of information and to integrate them in novel ways. Categories of information include (1) personal information input 31 by a user into the user profile ii such as date of birth, gender, height, weight, heart rate, blood pressure, relevant medical conditions such as diabetes and subjective state of mind and body; (2) user-specific health and performance data 40; (3) beverage dispensing history 33 including additives of beverages from the web domain; (4) geographic data 32 such as ambient temperature, humidity and altitude from third party providers, as well as user's own inputting as to whether her workout will be outside in the local environment or in an air-conditioned space; and (5) sentiment analysis obtained from several sources. Geographic information 32 includes altitude, temperature, humidity and/or presence of air conditioning, and can be obtained through the first or second web domains 9, 38. All of these categories of information are discussed herein.

The web domain collects a much richer and extensive set of beverage dispensing history than has existed before because this data is automatically tabulated from the user's own use of dispensers communicating with the web domain. The web domain collects data including volume and timing of intake, amount and type of beverage additives consumed such as caffeine, sugars, nutrients, vitamins and minerals, and electrolytes. These categories of information can be tracked in the web domain separately from flavor because the components can be dispensed separately from flavor. Additives may be selected from the group consisting of electrolytes, amino acids, proteins, sugars, flavoring, carbonation, caffeine, and CBD oil.

Sentiment analysis can be obtained from the user's own preferences and experiences in the web domain, or can be obtained by well known tools applied to social media domains. That is, when a large number of users of the web domain have distinct experience with a beverage, particularly its additives, then these positive or negative experiences can be factored into the RBI by the system 1. For example, users training for athletic events such as marathons and triathlons will post their reactions and opinions in social media sites which can be analyzed with tools such as those provided by 3rd party fee-for-service analytics firms like Hootsuite or natively using applications like Keyhole. Both of these examples offer configurable options to support an array of user-driving insights regarding sentiments expressed qualitatively by user experience. These insights can be leveraged in a novel way for the individual user to make informed choices regarding hydration decision that align with specific activity types in which he or she may engage. Additionally, insights derived from analytical sentiment analysis provided by the system may be valuable to beverage providers. In this context, product development and marketing may be tailored to the particular needs of product consumers in a uniquely specific and novel way to address heretofore unfulfilled expectations.

Third party research comprises data gathered from published and peer-reviewed third party research selected by the operator of the system 1. This information will receive a very favorable weighting within the data analytics module.

The data analytics system 41 is also configured to generate aggregated user information from user-specific beverage formulations and dispensing history 33 by aggregating data from multiple users in an anonymized and/or aggregated manner, the aggregated data being gathered from an account of a user or member. This data can be aggregated in order to provide input for an RBI to a first user, desirable options for beverages or additives to the operator of the web domain, or to generate individualized or aggregated analytics useful to beverage brands for advertising. This category can supplement third party research.

As discussed elsewhere herein, an additional user can assign a mandatory or suggested RBI to a first user. That is, if mandatory, the system is configured so that the first user's dispensing of a beverage will be limited to the RBI selected by the additional user but, if suggested, the first user will only receive a notification of the suggested RBI which can be selected or declined.

The data analytics system 41 is also configured to communicate with a data analytics database 45 in the web domain. As depicted in FIGS. 1-5 and 9, the data analytics database contains information about dispensing transactions including the dispenser's physical location (PLIN) such as type (e.g., commercial, home, healthcare, military), a physical location identification number (PLID), a dispenser ID, a timestamp, a user device identification number and/or whether the dispensing transaction was paid at a metered rate or under a subscription.

In one embodiment, the beverage dispenser gathers information about the dispenser from the diagnostic sensors including, as discussed herein. The dispenser sends data from the sensors over the first network connection 13 to a diagnostics module 36 within the web domain 9. An administrator of the system 1 (i.e., a person) may determine any work or repairs needed for a dispenser, prophylactically or after the fact.

In another embodiment the system 1 further comprises a touch screen to display available cartridges to a member or other user during a beverage session, and to enable a member or user to choose a beverage.

We claim:

1. A remote cartridge system for dispensing beverages comprising
   a. a stationary dispenser with a unique dispenser ID and comprising a pressurized dispenser water line, a controller, a first wireless reader and
      i. at least one first pairing unit comprising
         1. A beverage concentrate cartridge being replaceable and bearing specific cartridge data shareable through a cartridge antenna,
         2. A fluid connection between the beverage concentrate cartridge and a mixing manifold,
         3. A beverage pump fluidly connected to the beverage concentrate cartridge and the mixing manifold, and
         4. A second wireless reader on the dispenser configured to read the cartridge antenna and to transmit the specific cartridge data to the controller, and
      ii. at least one second pairing unit comprising a cleaning cartridge, a cleaning pump and an additional second wireless reader, and
   b. a first web domain comprising a transaction module and a mobile app downloadable onto a smart mobile device of a user synchronized with the first web domain and comprising an individual account comprising a user profile configured to hold profile information, the first web domain configured for a first network connection with the controller and a second network connection with the mobile app, and the mobile app configured to communicate with the controller by a smart mobile device antenna through the first wireless reader, and wherein the controller and the transaction module are configured to subtract from a beginning volume of the beverage concentrate cartridge a concentrate dose volume dispensed for each of the beverages and to calculate a running total of remaining volume of the beverage concentrate cartridge and the transaction module is further configured to send periodic instructions to the controller automatically to instruct the cleaning pump to release cleaner from the cleaning cartridge periodically to other components of the dispenser.

2. The system as in claim 1 wherein the profile information is selected from the group consisting of a unique user ID, a user's age, height, weight, gender, medical condition, fitness goals, planned exercise regimen and timing, beverage choices in a beverage selection queue and payment authorizations.

3. The system as in claim 2 wherein the beverage selection queue is configured to be preset before a transaction or revised during a dispensing session.

4. The system as in claim 3 wherein the first web domain, and the controller are further configured to match the specific cartridge data for each of the beverage concentrate cartridges with the beverage choices in the beverage selection queue and to generate and send instructions to at least one of the beverage pumps to pump the concentrate dose volume to the mixing manifold to make the beverage, and to store the transaction in a dispensing history.

5. The system as in claim 1 wherein the specific cartridge data is selected from the group consisting of the beginning volume, a concentrate mix ratio, a cleaning mix ratio, a unique cartridge ID, an ID for contents, expiration date, fill date and lot number.

6. The system as in claim 1 wherein the first wireless reader is configured for wireless communication with the mobile app through the smart mobile device antenna.

7. The system as in claim 1 wherein the transaction module is further configured to send notices for replacement cartridges to a system administrator, a cartridge fulfillment system and/or an inventory tracking system.

8. The system as in claim 1 wherein the first and the second wireless readers are selected from the group consisting of NFC, RFID, Bluetooth and WiFi, and the smart mobile device antenna and the cartridge antenna are compatible.

9. The system as in claim 4 wherein the first web domain and the mobile app further comprise a recommendation module configured to generate, from the profile information and the dispensing history, a recommended beverage intake (RBI) as a beverage recipe.

10. The system as in claim 9 further configured for an additional/leader network connection between the individual account and an additional portal to the first account, the additional portal configured to enable a second user to specify the RBI as mandatory or suggested, to make a custom recommendation for the user or to perform data analysis.

11. The system as in claim 1 wherein the dispenser further comprises at least one of a leak detector, a flow meter, a temperature sensor, a water pressure sensor communicating through the controller directly through the first network connection to a diagnostic module in the web domain.

12. A remote cartridge system for dispensing beverages comprising
  a. a stationary dispenser with a unique dispenser ID and comprising a pressurized dispenser water line, a controller, a first wireless reader and at least one first pairing unit comprising
    i. a beverage concentrate cartridge being replaceable and bearing specific cartridge data shareable through a cartridge antenna,
    ii. a fluid connection between the beverage concentrate cartridge and a mixing manifold,
    iii. a beverage pump fluidly connected to the beverage concentrate cartridge and the mixing manifold, and
    iv. a second wireless reader on the dispenser configured to read the cartridge antenna and to transmit the specific cartridge data to the controller, and
  b. a first web domain and a mobile app downloadable onto a smart mobile device of a user synchronized with the first web domain and comprising an individual account comprising a user profile configured to hold profile information, the first web domain configured for a first network connection with the controller and a second network connection with the mobile app, and the mobile app configured to communicate with the controller by a smart mobile device antenna through the first wireless reader, wherein the first web domain and the controller are further configured to match the specific cartridge data with beverage choices in a beverage selection queue and to generate and send instructions to at least one of the beverage pumps to pump the concentrate dose volume to the mixing manifold to make one of the beverages, and to store the transaction in a dispensing history, and wherein the first web domain and the mobile app further comprise a recommendation module configured to generate, from the profile information and the dispensing history, a recommended beverage intake (RBI) as a beverage recipe, and wherein user-specific health and performance information of the user is incorporated into the RBI, wherein user-specific health and performance information is collected by user input, an activity monitor or another other sensor and is found within:
    i. a training module in the first web domain or
    ii. a second web domain with a fourth network connection to or from the second web domain, wherein the user maintains a second account comprising the user-specific health and performance information.

13. The system as in claim 12 wherein the user-specific health and performance information is selected from the group consisting of length of exercise session, current or exercise session respiratory rate, resting heart rate, heart rate variability, quantity of sleep during a prior period, sleep performance during a prior period, volatile organic compounds from exhalation, biochemical levels in blood, interstitial fluid or cerebrospinal fluid, electro dermal activity, VO2 max, stress, caloric burn, training effect, power curve, functional threshold power, lactate level, lactate threshold, strain and recovery.

14. The system as in claim 1 wherein the cleaning cartridge and the cleaning pump are fluidly connected via a cleaning line to a flush reservoir.

* * * * *